United States Patent [19]
Rosen et al.

[11] Patent Number: 5,318,890
[45] Date of Patent: Jun. 7, 1994

[54] ASSAYS FOR INHIBITORS OF LEUKOCYTE ADHESION

[75] Inventors: Steven Rosen, San Francisco; Mark Singer, Berkeley; Yasuyuki Imai, San Francisco; Ted Yednock, Fairfax, all of Calif.

[73] Assignee: The Regents of the University of California, Oakland, Calif.

[21] Appl. No.: 695,805

[22] Filed: May 6, 1991

[51] Int. Cl.$^5$ .......................... C12Q 1/00; C12Q 1/02
[52] U.S. Cl. ................... 435/7.24; 435/7.1; 435/7.2; 435/7.92; 530/387.3
[58] Field of Search ................ 435/7.24, 7.1, 7.2, 435/7.92, 7.93; 530/388.73

[56] References Cited

PUBLICATIONS

Lasky, L. A., et al., "Cloning of a Lymphocyte Homing Receptor Reveals a Lectin Domain," *Cell* 56:1045–1055 (1989).
Gallatin, et al., "A cell-surface molecule involved in organ-specific homing of lymphocytes," *Nature* 304:30–34 (1983).
Siegelman, M. H., "Mouse Lymph Node Homing Receptor cDNA Clone Encodes a Glycoprotein Revealing Tandem Interaction Domains," *Science* 243:1165–1172 (1989).
Springer, T. A., "Adhesion receptors of the immune system," *Nature* 346:425–434 (1990).
Glabe, C. G., et al., "Preparation and Properties of Fluorescent Polysaccharides," *Anal. Biochem.* 130:287–294 (1983).
Imai, Y., et al, "Direct demonstration of the Lectin Activity of gp90$^{MEL}$, a Lymphocyte Homing Receptor," *J. Cell Biol.* 111:1225–1232 (1990).
Kishimoto, T. K., et al., "Neutrophil Mac-1 and MEL-14 Adhesion Proteins Inversely Regulated by Chemotactic Factors," *Science* 245:1238–1241 (1989).
Kishimoto, T. K., et al., "Identification of a human peripheral lymph node homing receptor: A rapidly down-regulated adhesion molecule," *Proc. Natl. Acad. Sci. USA* 87:2244–2248 (1990).
Spertini, O., et al., "Regulation of leukocyte migration by activation of the leukocyte adhesion molecule-1 (LAM-1) selectin," *Nature* 349:691–694 (1991).
Stoolman, L. M. and Rosen, S. D. "Possible Role for Cell-surface Carbohydrate-binding Molecules in Lymphocyte Recirculation," *J. Cell Biol.* 96:722–729 (1983).
Stoolman, L. M., et al., "Phosphomannosyl Receptors May Participate in the Adhesive Interaction between Lymphocytes and High Endothelial Venules," *J. Cell Biol.* 99:1535–1540 (1984).
Watson, S. R., et al., "Neutrophil influx into an inflammatory site inhibited by a soluble homing receptor-IgG chimaera," *Nature* 349:164–167 (1991).
Watson, S. R., et al., "A Homing Receptor-IgG Chimera as a Probe for Adhesive Ligands of Lymph Node High Endothelial Venules," *J. Cell Biol.* 110:2221–2229 (1990).
Willenborg, D. O. and Parish, C. R., "Inhibition of Allergic Encephalmoyelitis in Rats by Treatment with Sulfated Polysaccharides," *J. Immunol.* 140:3401–3405 (1988).
Willenborg, D. O., et al., "Phosphosugars are potent inhibitors of central nervous system inflammation," *FASEB J.* 3:1968–1971 (1989).
Yednock, T. A., et al., "Receptors Involved in Lymphocyte Homing: Relationship between a Carbohydrate-binding Receptor and the MEL-14 Antigen," *J. Cell Biol.* 104:725–731 (1987).
Yednock, T. A., et al., "Phosphomannosyl-derivatized Beads Detect a Receptor Involved in Lymphocyte Homing," *J. Cell Biol.* 104:713–723 (1987).

Primary Examiner—Richard A. Schwartz
Assistant Examiner—David Guzo
Attorney, Agent, or Firm—Karl Bozicevic

[57] ABSTRACT

The present invention provides novel assays for determining the ability of a test compound to inhibit intercellular adhesion mediated by a selectin receptor, such as the LHR. The assays involve contacting the test compound with the receptor and an isolated receptor-binding agent. The receptor-binding agent is a sulfated polysaccharide, a sulfated glycolipid, or a compound comprising the extracellular region of an endothelial cell surface glycoprotein. Also provided are compositions comprising a compound comprising the extracellular region of an endothelial cell surface protein, which is specifically recognized by lymphocyte homing receptors.

16 Claims, No Drawings

ASSAYS FOR INHIBITORS OF LEUKOCYTE ADHESION

This invention was made with support under Grant (or Contract) No. NIH GM-23547, awarded by the DHHS. The Government has certain rights in this invention.

BACKGROUND OF THE INVENTION

The present invention relates to compositions and methods for identifying compounds useful in the inhibition of cellular adhesion involved in a number of pathological responses. In particular, the invention relates to assays for inhibitors of a class of receptors which mediate leukocyte extravasation and other responses.

Recent work has established that specialized cell surface receptors (termed here selectins) on endothelial cells and various circulating cells are involved in a number of intercellular interactions. For instance, an adhesion molecule on the surface of leukocytes, lymphocyte homing receptor (LHR), is known to be involved in the adhesive interactions of leukocytes with the endothelial lining of blood vessels. This adhesive interaction is a prerequisite for the movement of leukocytes from the blood to tissue sites where immune reactions and inflammatory reactions occur.

LHR (also known as $gp90^{MEL}$, $gp100^{MEL}$, $gp110^{MEL}$, Mel-14 antigen, Leu8 antigen, TQ1 antigen, DREG antigen, LAM-1, selectin1, LECAM-1 and LEC-CAM-1, depending on animal species, leukocyte, and laboratory preference) is expressed on the surface of leukocytes, such as, lymphocytes, neutrophils, monocytes, and eosinophils (Gallatin, et al., *Nature* 303:30 (1983) and Lewinsohn, et al., *J. Immunol.* 138:4313 (1987), which are incorporated herein by reference). LHR is known to mediate the adhesion of lymphocytes to specialized endothelial cells in lymph nodes, leading to the migration of blood-borne lymphocytes into the lymph node. On neutrophils and monocytes, it mediates the early interaction of these cells with endothelium of blood vessels at sites of inflammation.

LHR is a lectin-like protein which performs its adhesive function by recognizing carbohydrate-containing ligands on endothelial cells. Lectin-like receptors have also been found on endothelial cells and platelets. Endothelial leukocyte adhesion molecule-1 (ELAM-1) is present on endothelial cells and is involved in the recognition of various circulating cells by the endothelium. Granule membrane protein-140 (GMP-140) is present on the surface of platelets and endothelial cells, where it mediates platelet-leukocyte and endothelium-leukocyte interactions.

Recent work has established that these receptors share certain structural features. Each of the receptors in this class is a glycoprotein with a lectin-like domain, a region with homology to epidermal growth factor, and a region with homology to complement regulatory proteins (see, Springer, *Nature*, 346:425, 1989, which is incorporated herein by reference). The term "selectin" is used herein to refer to this class of lectin-like receptors.

There is currently an interest in developing highly specific competitive inhibitors of selectin-mediated cellular adhesion. Such inhibitors are useful in therapeutic regimens to treat various selectin-mediated disease responses. The inhibitors could also be used to target other pharmaceutical compounds, such as anti-inflammatory agents or anti-oxidants, to the sites of injury.

To date, however, insufficient understanding of the interaction of selectin receptors and their ligands has hindered these efforts. In addition, the prior art lacks rapid, economical methods for identifying inhibitors of selectin-mediated interactions. For example, in vitro intercellular adhesion assays have been used to test inhibition (see, e.g., Stamper and Woodruff, *J. Exp. Med.* 144:828-833 (1976), which is incorporated herein by reference). These assays, however, are difficult to carry out and do not lend themselves to screening large numbers of test compounds. Also, comparisons of active compounds by quantitative dose-response studies is difficult using these assays. The present invention addresses these and related needs.

SUMMARY OF THE INVENTION

The present invention provides novel assays for determining the ability of a test compound to inhibit intercellular adhesion mediated by a selectin receptor, such as the LHR. The assays involve contacting the test compound with the receptor and an isolated receptor-binding agent. The receptor-binding agent is a phosphorylated polysaccharide, a sulfated polysaccharide, a sulfated glycolipid, or a compound comprising the extracellular region of an endothelial cell surface glycoprotein. The agent is preferably PPME, fucoidin, dextran sulfate, or a compound comprising the extracellular region of $Sgp^{50}$ or $Sgp^{90}$.

The assays are typically carried out in a cell-free environment in which either the receptor or receptor-binding agent is immobilized on a solid surface. The assays may also be performed using intact cells and a fluorescence activated cell sorter. The ability of the test compound to inhibit binding between the receptor and the agent is detected in a number of ways, typically by using a labeled receptor binding agent.

Also disclosed are compositions comprising the extracellular region of an endothelial cell surface glycoprotein. The extracellular region comprises a carbohydrate ligand specifically recognized by LHR. The glycoprotein is typically $Sgp^{50}$ or $Sgp^{90}$.

Finally, compositions comprising inhibitor compounds identified by the above methods are disclosed. The inhibitors can be used in pharmaceutical compositions to treat various selectin-mediated disease states.

DESCRIPTION OF THE PREFERRED EMBODIMENTS

The present invention provides novel assays useful in identifying inhibitors of selectin-mediated intercellular adhesion. Also provided are isolated endothelial cell surface glycoproteins which selectively bind lymphocyte homing receptors. Compounds comprising the extracellular region of these glycoproteins are particularly useful in the assays of the present invention.

As discussed above, selectins, also known as the "LEC-CAM" family of cell adhesion molecules, are unique cell surface glycoproteins. These receptors are involved in a variety of intercellular interactions. For instance, the trafficking of lymphocytes from-the blood into secondary lymphoid organs, such as lymph nodes and gut-associated Peyer's patches, is known to be initiated by an adhesive interaction between specialized endothelial cells of high endothelial venules (HEV) and LHRs on lymphocytes. Berg et al., *Immunol. Rev.* 108:5-18 (1989); Duijvestijn and Hamann, *Immunol.*

*Today* 10:23-28 (1989); Woodruff et al., *Ann. Rev. Immunol.* 5:201-222 (1987); Yednock and Rosen, *Adv. Immunol.* 54:313-378 (1989); Stoolman, *Cell* 56:907-910 (1989); Gallatin et al., *Cell* 44:673-680 (1986); Rosen, *Curr. Opin. Cell. Biol.* 1:913-919 (1989), all of which are incorporated herein by reference.

The endothelial ligands recognized by LHR molecules are postulated to be distinctive for the different lymphoid organs and as such are proposed to be responsible for regulating the lymphocyte populations that enter each class of lymphoid organ. Strong support for organ-specific HEV determinants has come with the discovery of the mouse "vascular addressin" antigens, defined by the panel of MECA monoclonal antibodies (Streeter et al., *Nature* 331:41-46 (1988) and Streeter et al., *J. Cell Biol.* 107:1853-1962 (1988) both of which are incorporated herein by reference).

The lectin domain on LHR for lymph nodes in humans and mice was initially inferred based upon the ability of specific phosphorylated monosaccharides, such as mannose-6-phosphate (M6P), and specific polysaccharides to prevent lymphocyte attachment to HEV (Stoolman and Rosen, *J. Cell Biol.* 96:722-729 (1983); Stoolman et al., *J. Cell Biol.* 99:1535-1540 (1984); Yednock et al., *J. Cell Biol.* 104:713-723 (1987); Stoolman et al., *Blood* 70:1842-1850 (1987); Stoolman and Ebling, *J. Clin. Invest.* 84:1196-1205 (1989) all of which are incorporated herein by reference). Notable among the active polysaccharides are PPME (a phosphate-rich mannan core) and fucoidin (a sulfated, fucose-rich polymer). This carbohydrate-binding activity depends on the presence of calcium, which is also required for the attachment of lymphocytes to HEV.

From the lectin nature of LHR, the ligands on lymph node HEV are presumed to bear a carbohydrate-based recognition determinant. Early studies demonstrated that the adhesive sites on peripheral lymph node HEV are periodate sensitive (Rosen et al., *Science* 228:1005-1007 (1985) which is incorporated herein by reference), indicating a requirement for carbohydrate. Subsequently, it was demonstrated that sialidase treatment of HEV, in vitro or in vivo, selectively eliminates lymphocyte attachment to peripheral lymph node HEV but has no effect on the binding to Peyer's patch HEV (Rosen et al., *J. Immunol.* 142:1895-1902 (1989) which is incorporated herein by reference). In addition, exposure of peripheral lymph node tissue sections to Limax flavus agglutinin, a sialic acid-specific lectin, prevents lymphocyte attachment to HEV (True et al., *J. Cell Biol.* 111:2757-2764 (1990) which is incorporated herein by reference).

The biochemical nature of the ligands, however, has not been defined. Adhesion-blocking activity and selective staining of peripheral lymph node HEV have been shown by MECA-79, a monoclonal antibody which apparently recognizes a complex of HEV cell surface proteins (EPO Publication No. 0303463 and Butcher, *Am. J. Pathol.* 136:3-12 (1990) which are incorporated herein by reference). The present invention provides the first evidence that LHR specifically binds a surface glycoprotein recognized by this antibody. In particular evidence provided here establishes that LHR recognizes a sulfated, fucosylated and sialylated glycoprotein of about 50 kd. A glycoprotein of 90 kd with similar characteristics is also identified.

Other selectins have also been extensively studied. ELAM-1 is inducibly expressed on vascular endothelial cells (Bevilacqua et al., *Science* 243:1160 (1989) and Hession et al., *Proc. Nat'l. Acad. Sci.,* 87:1673 (1990), both of which are incorporated herein by reference). This receptor has been demonstrated to be induced by inflammatory cytokines such as interleukin $I\beta$ (IL-$I\beta$) and tumor necrosis factor $\alpha$ (TNF$\alpha$), as well as bacterial endotoxin (lipopolysaccharide) (see, Bevilacqua et al., *Proc. Natl. Acad. Sci.,* 84:9238-9242 (1987) which is incorporated here y reference). These compounds act directly on endothelial cells in vitro to substantially augment polymorphonuclear leukocyte (neutrophil), and monocute adhesion (Bevilacqua et al., *Proc. Natl. Acad. Sci.,* supra). Detailed structures have been proposed for an oligosaccharide moiety recognized by ELAM-1 (Philips et al. *Science* 250:1130-1132 (1990) and Walz et al. *Science* 250:1132-1135 (1990), both of which are incorporated herein by reference).

A third member of the selectin family, GMP-140, is a membrane glycoprotein of platelet and endothelial secretory granules (Geng et al., *Nature,* 343, 757-760 (1990) which is incorporated herein by reference). Activated platelets which express GMP-140 on their surface are known to bind to monocytes and neutrophils (Jungi et al., *Blood* 67:629-636 (1986)), and also to monocyte-like cell lines, e.g., HL60 and U937 (Jungi et al., supra; Silverstein et al., *J. Clin. Invest.* 79:867-874 (1987)), all of which are incorporated herein by reference. GMP-140 is an alpha granule membrane protein of molecular weight 140,000 that is expressed on the surface of activated platelets upon platelet stimulation and granule secretion (Hsu-Lin et al., *J. Biol. Chem.* 259:9121-9126 (1984); Stenberg et al., *J. Cell Biol.* 101:880-886 (1985); Berman et al., *J. Clin. Invest.* 78:130-137 (1986)). It is also found in megakaryocytes (Beckstead et al., *Blood* 67:285-293 (1986)), and in endothelial cells (McEver et al., *Blood* 70:355a (1987)) within the Weibel-Palade bodies (Bonfanti et al., *Blood* 73:1109-1112 (1989)). Furie et al. U.S. Pat. No. 4,783,330, describe monoclonal antibodies reactive with GPM-140. All of the foregoing references are incorporated herein by reference.

The structure and function of selectin receptors has been elucidated by cloning and expression of full length cDNA encoding each of the above receptors (see, e.g., Bevilacqua et al., *Science,* supra, (ELAM-1), Geng et al., supra, (GMP 140), and Lasky et al., *Cell* 56:1045-1055 (1989) (LHR) which is incorporated herein by reference). The extracellular portion of selectins can be divided into three segments based on homologies to previously described proteins. The N-terminal region (about 120 amino acids) is related to the C-type mammalian lectin protein family as described by Drickamer, *J. Biol. Chem.,* 263: 9557-9560 (1988) (which is incorporated herein by reference) that includes low affinity IgE receptor CD23. A polypeptide segment follows, which has a sequence that is related to proteins containing the epidermal growth factor (EGF) motif. Lastly, after the EGF domain are one or more tandem repetitive motifs of about 60 amino acids each, related to those found in a family of complement regulatory proteins.

In one aspect, the present invention is directed to methods for assaying test compounds for the ability to inhibit selectin-mediated responses. Ideally, the assays of the present invention allow large scale in vitro screening of a variety of compounds.

Inhibition of a number of binding interactions can be assayed. For instance, inhibition of the binding between a monoclonal antibody and an isolated selectin receptor can be used. Numerous types of competitive assays involving immunoglobulins are known (see, e.g., U.S. Pat. Nos. 3,376,110, 4,016,043, and Harlow and Lane, *Antibodies: A Laboratory Manual*, Cold Spring Harbor Publications, N.Y. (1988), which are incorporated herein by reference).

The in vitro assays of the present invention are typically assays which detect the ability of a test compound to inhibit binding between the receptor and an isolated receptor-binding agent. The term "isolated receptor-binding agent" is used to refer to an agent that is not associated with an intact cell membrane. Thus, intact cells which express ligand molecules recognized by selectin receptors are not used in the assays of the present invention. The receptor-binding agents are typically prepared from appropriate cells according to standard methods, purchased in a purified state, or synthetically produced. Although the agents are not associated with intact cell membranes they may be associated with cell membrane fragments or incorporated into artificial lipid membranes (e.g. liposomes).

Unlike prior art methods, the present assays are not based on measuring the presence or absence of intercellular adhesion but are typically carried out in a cell-free environment. The term "a cell-free environment" is used here to indicate that intact cells are substantially absent from the assay. The assay is considered to be cell-free despite the presence of cellular debris or cell membrane fragments which comprise a component of the assay. In some formats, however, (e.g. those using a fluorescence activated cell sorter) intact cells, such as lymphocytes, which express the receptor of interest are used.

A number of compounds known to block intercellular adhesion can be used as the receptor-binding agent in the present invention. For instance, phosphorylated monosaccharides, such as mannose-6-phosphate and fructose-1-phosphate inhibit lymphocyte attachment to HEV in in vitro cellular assays. Polysaccharides and glycolipids, have also been shown to inhibit in vitro binding of these cells (Stoolman et al., supra; Yednock et al., supra, and Yednock et al., *J. Cell Biol.*, 104:725–731 (1987), which is incorporated herein by reference.

The polysaccharides of the present invention are phosphorylated or sulfated. Phosphorylated polysaccharides include the phosphomannan monoester core from Hansenula hostii (PPME). Sulfated polysaccharides include fucoidin and dextran sulfate. Sulfated glycolipids of the invention include sulfatide. Using the novel assays claimed here, however, one of skill can easily identify other polysaccharides and glycolipids within the scope of the claims which are effective receptor-binding agents. For instance, Example 1, below, provides a method suitable for assaying such compounds. The results provided there indicate that different compounds have different inhibitory activities.

Receptor-binding agents of the present invention can be easily prepared from commonly available starting materials. Polysaccharides and glycolipids are isolated from animal, plant, fungal or prokaryotic cells according to standard techniques. For instance, PPME is purified from crude yeast mannan by the method of Slodki et al., *Biochim. Biophys. Acta*, 304:449–456 (1973), which is incorporated herein by reference. Briefly, the phosphomannan is acid hydrolyzed. After neutralization, the phosphomannan core is precipitated and rehydrated in water. Contaminating protein is removed by water:-chloroform:butanol extraction. The compounds can also be chemically synthesized according to standard techniques (see, e.g., Khadem, *Carbohydrate Chemistry* (Academic Press, San Diego, Calif., 1988), which is incorporated herein by reference. Alternatively, many polysaccharides (such as fucoidin) and glycolipids can be purchased from chemical supply companies, such as Sigma Chemical Co. (St. Louis, Mo.) and Aldrich Chemical Co. (Milwaukee, Wisc.).

The selectin receptor used in the assays of the present invention may or may not be associated with an intact cell. Typically, the receptor is purified from its native environment before use in the assay. As discussed above, cDNA encoding each of the selectin receptors has been isolated. Thus, the receptors can be recombinantly produced using standard methods well known to those skilled in the art. For a review of standard molecular biological techniques see Sambrook et al., *Molecular Cloning: A Laboratory Manual*, 2d Ed. (Cold Spring Harbor Press, N.Y., 1989), which is incorporated herein by reference. In addition, using standard recombinant DNA techniques, mutations can be induced to obtain proteins with altered amino acid sequences. Typically, substitutions, deletions or additions are introduced which provide desired characteristics. For instance, increased solubility can be achieved by elimination of the hydrophobic transmembrane region of the protein. In addition, soluble chimeric receptors comprising the constant region of an immunoglobulin molecule can also be produced (Watson et al., *J. Cell Biol.* 110:2221–2229 (1990), and Watson et al., *Nature* 349:164–167 (1991) which are incorporated herein by reference).

The test compound to be screened will usually be a synthetic or naturally-produced biomolecule, such as a carbohydrate (e.g., oligosaccharide) or glycoconjugate. It can also be a peptide, polypeptide, protein (e.g., monoclonal antibody), nucleic acid, and the like. The test compound is typically a relatively small molecule with a molecular weight less than about 10 kD, preferably less than about 5 kD. The compounds are synthetically produced using standard methods for synthesizing oligosaccharides (Khadem, supra). Methods for synthesizing polypeptides of defined composition are well known in the art (see, Atherton et al. *Solid Phase Peptide Synthesis* (IRL Press, Oxford, 1989) which is incorporated herein by reference). If the synthetic test compounds are polymeric (e.g., polypeptides or polysaccharides) they are preferably altered in a systematic way to identify the sequence of monomers which have the desired effect (see, e.g., U.S. Pat. No. 4,833,092, which is incorporated herein by reference). Test compounds may also be isolated from any natural source, such as animal, plant, fungal, or prokaryotic cells in accordance with standard procedures.

The assays of the present invention are particularly useful in identifying compounds which act as antagonists of a ligand molecule. Antagonists are compounds which reverse the physiological effect of a ligand or exclude binding of the ligand to the receptor. An antagonist competes directly or indirectly with the ligand for the receptor binding site and, thus, reduces the proportion of ligand molecules bound to the receptor. Typically, an antagonist will be the topographical equivalent of the natural ligand and will compete directly with the ligand for the binding site on the selectin. Such a compound is referred to here as a "mimetic." A ligand mimetic is a molecule that conformationally and functionally serves as substitute for the natural ligand recognized by a selectin receptor. Alternatively, if the ligand and the test compound can bind the receptor simultaneously, the compound may act non-competitively. A non-competitive inhibitor acts by decreasing or inhibiting the subsequent physiological effects of receptor-ligand interactions rather than by diminishing the proportion of ligand molecules bound to the receptor.

The assays of the present invention can also be used to identify synthetic or naturally occurring agonists. Agonists are compounds which bind the receptor and initiate a physiological response similar to that of the natural ligand.

The inhibitors of selectin-ligand interaction identified by the assays of the present invention are useful in treating a number of selectin-mediated disease responses. For instance, selectins play an important role in recruitment of leukocytes to the sites of injury, particularly inflammation. The inhibitors therefore may be administered locally or systemically to control tissue damage associated with such injuries. Moreover, because of the specificity of such inhibitors for sites of inflammation, these compositions will be more effective and less likely to cause complications when compared to traditional anti-inflammatory agents.

Pharmaceutical compositions comprising the inhibitors can be used to block or inhibit cellular adhesion associated with a number of disorders. For instance, a number of inflammatory disorders are associated with selectins expressed on vascular endothelial cells and platelets. The term "inflammation" is used here to refer to reactions of both the specific and non-specific defense systems. A specific defense system reaction is a specific immune system reaction to an antigen. Examples of specific defense system reactions include antibody response to antigens, such as viruses, and delayed-type hypersensitivity. A non-specific defense system reaction is an inflammatory response mediated by leukocytes generally incapable of immunological memory. Such cells include macrophages, eosinophils and neutrophils. Examples of nonspecific reactions include the immediate swelling after a bee sting, and the collection of PMN leukocytes at sites of bacterial infection (e.g., pulmonary infiltrates in bacterial pneumonias and pus formation in abscesses).

Other treatable disorders include, e.g., rheumatoid arthritis, post-ischemic leukocyte-mediated tissue damage (reperfusion injury), frost-bite injury or shock, acute leukocyte-mediated lung injury (e.g., adult respiratory distress syndrome), asthma, traumatic shock, septic shock, and acute and chronic inflammation, including atopic dermatitis, psoriasis, and inflammatory bowel disease. Various platelet-mediated pathologies such as atherosclerosis and clotting can also be treated. In addition, tumor metastasis can be inhibited or prevented by inhibiting the adhesion of circulating cancer cells. Examples include carcinoma of the colon and melanoma.

Thus, the present invention also provides pharmaceutical compositions which can be used in treating the aforementioned conditions. The pharmaceutical compositions are comprised of inhibitory compounds together with pharmaceutically acceptable carriers. The pharmaceutical compositions can be prepared according to standard methods (see *Remington's Pharmaceutical Sciences*, Mack Publishing Co., Philadelphia, Pa., 19th ed. (1985) which is incorporated herein by reference). The pharmaceutical compositions are suitable for use in a variety of drug delivery systems. For a brief review of present methods for drug delivery, see, Langer, *Science* 249:1527–1533 (1990), which is incorporated herein by reference.

In one embodiment, the inhibitors can be used to target conventional anti-inflammatory drugs or other agents to specific-sites of tissue injury. By using a selectin-binding moiety to target a drug to a selectin receptor on, e.g., a vascular endothelial cell, such drugs can achieve higher concentrations at sites of injury. Side effects from the conventional anti-inflammatory agents can be substantially alleviated by the lower dosages, the localization of the agent at the injury sites and/or the encapsulation of the agent prior to delivery. Targeting can be achieved by directly or indirectly linking the inhibitor to the anti-inflammatory agent. For instance, liposomes filled with the anti-inflammatory agent can be constructed which incorporate the inhibitor in the lipid membrane (see, Langer, supra). When the liposomes are brought into proximity of the affected cells, they deliver the elected therapeutic compositions.

The pharmaceutical compositions containing the inhibitors can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as a "therapeutically effective dose." Amounts effective for this use will, of course, depend on the severity of the disease and the weight and general state of the patient.

In prophylactic applications, compositions containing the inhibitors are administered to a patient susceptible to or otherwise at risk of a particular disease. Such an amount is defined to be a "prophylactically effective dose." In this use, the precise amounts again depend on the patient's state of health and weight.

The present invention also provides lymph node endothelial cell surface sulfated glycoproteins which comprise oligosaccharide biological ligands specifically recognized by LHR for lymph nodes. As described more fully below, two such glycoproteins, $Sgp^{50}$ and $Sgp^{90}$, have been identified. Having identified ligand-bearing glycoproteins, one of skill will recognize that a number of modifications of the glycoproteins that do not significantly alter the LHR binding activity are possible. Such modifications include enzymatic or chemical treatment of the proteins to produce fragments that comprise the carbohydrate ligand recognized by LHR. For instance, fragments of the extracellular region of the proteins can be obtained by treatment of the isolated glycoproteins with an appropriate protease such as trypsin, pronase, papain, pepsin and the like.

The extracellular region of the cell surface glycoproteins includes all sequences from the proteins outside the transmembrane and intracellular regions. The extracellular region of the glycoproteins of the present invention comprises a carbohydrate ligand specifically recognized by LHR. The extracellular region may also contain sequences from the transmembrane region (less than about 10 amino acids), so long as solubility is not substantially affected. The term "compound comprising the extracellular region" includes any compound in which the extracellular region, or fragment thereof, is conjugated to a second moiety. The term also embraces the isolated extracellular region and the isolated full length glycoprotein. An "isolated compound comprising the extracellular region" includes such a compound (e.g., a full length glycoprotein) in other than its native state, that is, not associated with an endothelial cell. For instance, the compound may be recombinantly produced, solubilized from the appropriate cell, or associated with a liposome.

Analysis of sulfated the glycoproteins of the present invention has revealed that the oligosaccharide moieties recognized by LHR are O-linked. Thus, they can be cleaved from the protein backbones by beta elimination and borohydride reduction according to standard techniques (see, e.g., Fukuda, *Meth. Enzymol.* 179:17–29 (1989), which is incorporated herein by reference).

The sulfated glycoproteins, or fragments thereof, can be isolated using soluble LHR as described below. The isolated soluble molecules are then used in the assays of the present invention. These molecules are particularly useful in the invention because inhibition of the interaction of the LHR with the actual biological ligand is assayed. The glycoproteins are also suitable as inhibitors of LHR-mediated cellular adhesion in the pharmaceutical compositions, described above. In either case, the glycoproteins can be used as they are isolated or they can be conjugated to a variety of other compounds to confer any number of desired characteristics, such as improved solubility, serum half-life and the like. Alternatively, neoglycoproteins or neoglycolipids can be prepared based on the carbohydrate chains of the glycoproteins using methods well known in the art (see, e.g., Stowell et al., *Adv. Carb. Chem and Biochem.* 37:225–281 (1980) and Childs et al. *Biochem. J.,* 262:131–138 (1989), which are incorporated herein by reference.)

In the assays of the present invention, any component of the assay, typically the receptor, is bound to a solid surface. For instance, in the case of LHR-based assays, purified LHR is coated on a solid surface and the ability of the test compound to inhibit binding between the receptor and a LHR-binding agent is detected.

Many methods for immobilizing biomolecules on solid surfaces are known in the art. For instance, the solid surface may be a membrane (e.g., nitrocellulose), a microtiter dish (e.g., PVC or polystyrene) or a bead. The desired component may be covalently bound or noncovalently attached through unspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), silicones, polyformaldehyde, cellulose, cellulose acetate, nitrocellulose, etc. other materials which may be employed, include paper, glasses, ceramics, metals, metalloids, semiconductive materials, cermets or the like. In addition are included substances that form gels, such as proteins, e.g., gelatins, lipopolysaccharides, silicates, agarose and polyacrylamides or polymers which form several aqueous phases, such as dextrans, polyalkylene glycols (alkylene of 2 to 3 carbon atoms) or surfactants e.g. amphophilic compounds, such as phospholipids, long chain (12–24 carbon atoms) alkyl ammonium salts and the like. Where the solid surface is porous, various pore sizes may be employed depending upon the nature of the system.

In preparing the surface, a plurality of different materials may be employed, particularly as laminates, to obtain various properties. For example, protein coatings, such as gelatin can be employed to avoid nonspecific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See for example Chibata, *Immobilized Enzymes,* Chibata, Halsted Press, New York, 1978, and Cuatrecasas, *J. Biol. Chem.* 245:3059 (1970) which are incorporated herein by reference.

In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as Concanavalin A will bind a carbohydrate containing compound but not a labeled protein that lacks glycosylation. Various solid surfaces for use in noncovalent attachment of assay components are reviewed in U.S. Pat. Nos. 4,447,576 and 4,254,082, which are incorporated herein by reference.

Many assay formats employ labeled assay components, typically the selectin-binding agent. The label may be coupled directly or indirectly to the desired component of the assay according to methods well known in the art. A wide variety of labels may be used. The component may be labeled by any one of several methods. A common method of detection is the use of autoradiography with $^3H$, $^{125}I$, $^{35}S$, $^{14}C$, or $^{32}P$ labeled compounds or the like. The choice of radioactive isotope depends on research preferences due to ease of synthesis, varying stability, and half lives of the selected isotopes. Other non-radioactive labels include ligands which bind to labeled antibodies, fluorophores, chemiluminescent agents, enzymes, and antibodies which can serve as specific binding pair members for a labeled ligand. The choice of label depends on sensitivity required, ease of conjugation with the compound, stability requirements, and available instrumentation.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. Ligands and anti-ligands may be varied widely. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various signal producing systems which may be used, see, U.S. Pat. No. 4,391,904, which is incorporated herein by reference.

In other embodiments, a fluoresence-activated cell sorter (FACS) is used to isolate selectin bearing cells and quantify inhibitory effects of test compounds. Typically, receptor-binding agents are labeled with a fluorescent compound and the amount of labeled agent bound to the cell surface is determined by flow cytometry. In the FACS, a stream of cells flows past a laser beam which causes the labeled cells to emit light. The stream is broken into droplets, each containing a single cell. Droplets containing a fluorescent cell are given a charge, which allows them to be separated from droplets containing no cell or an unlabeled cell. In addition, to sorting the apparatus can be used to measure the level of fluorescence in labeled cells. For a general discussion of fluorescence activated cell sorting and flow cytometry see Parks et al., in *Fundamental Immunology*, Paul, ed. (Raven Press, 2d. ed. 1989), which is incorporated herein by reference.

In the assays of the present invention, fluorescent-labeled agents (such as PPME and fucoidin) are used to detect selectin receptors on cells such as leukocytes, platelets, and endothelial cells. For instance, flow cytometry can be used to detect LHR on viable lymphocytes and inhibitors can be easily determined. In addition, a quantitative measure of a receptor's activity on a cell surface can be determined.

The following examples are offered by way of illustration, not by way of limitation.

EXAMPLE 1

PPME-based ELISA Assay with Anti-PPME Antibody

This example shows the ability of assays of the present invention to identify inhibitors of LHR-mediated intercellular adhesion. The illustrated assay uses LHR coated on the wells of microtiter plates. Binding of PPME to the coated wells is detected with a rabbit antibody to PPME.

To perform the assay, LHR for lymph nodes purified by immunoaffinity chromatography as previously described (Lasky et al. supra; Geoffroy and Rosen, *J. Cell Biol.* 109:2463-2469 (1989) which is incorporated by reference) was equilibrated in Dulbecco's PBS (0.68 mM calcium, 0.49 mM magnesium) containing either 1 mM CHAPS or 40 mM octylβ-D-glucopyranoside. The PPME-binding activity of LHR appeared to be more stable in octylβ-D-glucopyranoside than in CHAPS.

10 µl of LHR solution at specified concentrations was diluted into 90 µl of PBS in the wells of Immulon-2 microtiter plates (Dynatech Laboratories, Inc., Chantilly, Va.). The dilution factor was chosen to reduce the detergent concentration below the critical micellar concentration. Adsorption was allowed to proceed overnight at 4° C. The wells were washed three times with PBS containing 0.1% Tween 20 (PBS-Tween). 200 µl of PBS containing 3% BSA and 0.02% NaN$_3$ was then added to each well to block nonspecific binding sites.

After a 2-h incubation at 22° C. with agitation, the wells were washed and then received 100 µl of PPME in 3% BSA-PBS or 3% BSA-PBS alone (control for background). After a 1-h incubation at 4° C., the wells were washed to remove unbound polysaccharide and 100 µl of rabbit anti-PPME antiserum (1:100 dilution into 3% BSA in PBS-Tween) was added to each well. Anti-PPME antiserum was prepared by injection New England white rabbits with 100 µg of PPME emulsified in 2 ml Freund's complete adjuvant: (Difco Laboratories, Detroit, Mich.). The antigen was administered in multiple intradermal and subcutaneous sites.

The incubation of the test compound in the presence of LHR and PPME and all subsequent incubations were allowed to proceed at 22° C. with agitation. After 1 h of exposure to anti-PPME, the wells were washed and 100 µl per well of biotinylated goat anti-rabbit IgG (1:200 dilution into 3% BSA in PBS-Tween) was added and allowed to react for 1 h. The wells were again washed before the addition of 50 µl per well of Vector ABC-AP reagent in PBS-Tween made according to the manufacturer's specifications. After 30 min., the wells were washed again and color development was initiated by the addition of 100 µl per well of substrate solution (p-nitrophenylphosphate, 1 mg/ml in 10% [vol/vol] diethanolamine-HCl buffer, pH 9.8).

Optical density readings were made at 405 nm with a microplate reader (BioRad Laboratories, Model 3550; Richmond, Calif.). Mean values are determined for two to three replicate wells. With PPME added in excess, a saturation level of binding was observed at $\geq 0.4$ µg of LHR per well.

In assays measuring the ability of test components to compete with PPME for binding to immobilized LHR, a concentration of 0.2-0.5 µg per well of LHR was added and the substances (diluted into 50 µl of PBS) were allowed to react with the antigen for 1 h at 4° C. PPME (50 µl, in 6% BSA-PBS) was added to each well, and the plate was incubated for an additional 1 h at 4° C. The plate was then processed as described above.

The concentrations of the test compounds are expressed as final concentrations after addition of the PPME. To test lipids as inhibitors, samples dissolved in chloroform-methanol 1:1 were dried in glass test tubes under a stream of nitrogen, and then suspended in PBS by brief sonication (model D-50; Branson Sonic Power Co., Chicago, Ill.). All of the inhibitory effects documented in this example were observed in two independent experiments. The ability of the assay to defect the inhibitory effects of various test compounds is presented in Tables 1 and 2.

TABLE 1

Inhibitory Activities of Sulfated Macromolecules

| Substance | Concentration for 50% inhibition µg/ml |
| --- | --- |
| sulfatide (Matreya, Inc.) | ND |
| sulfatide (Sigma Chemical Co.) | 0.7-1.3 |
| cholesterol-3-sulfate | >100 |
| chondroitin sulfate A | >1,000 |
| chondroitin sulfate B | >1,000 |
| chondroitin sulfate C | >1,000 |
| keratan sulfate | >1,000 |
| fucoidin (Sigma Chemical Co.) | ND |
| heparan sulfate | >1,000 |
| fucoidin (CN K&K Laboratories) | 0.1-0.4 |
| heparin (porcine intestinal) | 100 |
| heparin (bovine lung) | 19 |
| heparin (porcine mucosa) | 110 |
| egg jelly fucan | 0.2 |

TABLE 1-continued

Inhibitory Activities of Sulfated Macromolecules

| Substance | Concentration for 50% inhibition μg/ml |
|---|---|
| polyvinylsulfate | >1,000 |

TABLE 2

Effects of Lipids on PPME Binding to LHR

| Experiment | Inhibitor | μg/ml | OD 405 nm |
|---|---|---|---|
| 1 | None | — | 0.596 ± 0.025 |
|  | Sulfatide (Sigma Chemical Co.) | 10 | 0.030 ± 0.005 |
|  | Sulfatide (Metreya, Inc.) | 10 | 0.019 ± 0.006 |
|  | Galactosylceramide | 10 | 0.668 ± 0.021 |
|  | Gal(6-SO$_4$)β1-1 Cer | 10 | 0.612 ± 0.016 |
|  | Cholesterol 3-SO$_4$ | 10 | 0.583 ± 0.014 |
| 2 | None | — | 0.291 ± 0.065 |
|  | Sulfatide (Sigma Chemical Co.) | 10 | 0.023 ± 0.018 |
|  | G$_{M1}$ | 10 | 0.208 ± 0.014 |
|  | G$_{D1a}$ | 10 | 0.328 ± 0.017 |
|  | G$_{D1b}$ | 10 | 0.256 ± 0.053 |
|  | G$_{T1b}$ | 10 | 0.287 ± 0.017 |
| 3 | None | — | 0.362 ± 0.064 |
|  | Sulfatide (Matreya, Inc.) | 100 | 0.0 |
|  | G$_{M1}$ | 100 | 0.301 ± 0.026 |
|  | G$_{M2}$ | 100 | 0.248 ± 0.042 |
|  | G$_{Me}$ | 100 | 0.378 ± 0.019 |
| 4 | None | — | 0.431 ± 0.047 |
|  | Sulfatide (Matreya, Inc.) | 10 | 0.0 |
|  | G$_{D1a}$ | 100 | 0.331 ± 0.025 |
|  | G$_{D1b}$ | 100 | 0.313 ± 0.011 |
|  | G$_{T1b}$ | 100 | 0.257 ± 0.026 |
|  | G$_{D3}$ | 100 | 0.555 ± 0.021 |
|  | G$_{Q1b}$ | 100 | 0.288 ± 0.032 |

Structures of the Glycolipids tested in Table 2 are as follows: Galactosylceramide, Galβ1-1Cer; Sulfatide, Gal(3-SO$_4$)β1-1Cer; G$_{M1}$, Galβ1-3GalNAcβ1-4[NeuSAcα2-3]Galβ1-4Glcβ1-1Cer; G$_{D1a}$, NeuAcα2,-3Galβ1-3GalNacβ11-4[NeuAcα2-3]Galβ1-4Glcβ1-1Cer; G$_{D1b}$, Galβ1-3GalNAcβ1-4[NeuAcα2-8NeuAcα2-3]Galβ1-4Glcβ1-1Cer; G$_{T1b}$, NeuAcα2-3GalNAcβ1-4[NeuAcα2-8NeuAcα2-3]Galβ1-4Glccβ1-1Cer; G$_{M2}$, GalNacβ11-4[NeuAcα2-3]Galβ1-4Glcβ1-1Cer; G$_{M3}$ NeuAcα2-3Galβ1-4Glcβ1-1Cer; G$_{D3}$, NeuAcα2-8NeuAcα2-3Galβ1-4Glcβ1-1Cer; G$_{Q1b}$, NeuAcα2-8NeuAcα2-3Galβ1-3GalNAcβ1-4[NeuAcα2-8NeuAcα2-3]Galβ1-4Glcβ1-1Cer. Three replicates were performed with each glycolipid.

EXAMPLE 2

ELISA Assay with fluoresceinated-PPME or fluoresceinated-fucoidin

In this assay, native or recombinant LHR was coated onto plastic wells of an ELISA plate as in assay 1 above. A fluorescein conjugate of either PPME (i.e., fl-PPME) or of fucoidin (fl-fucoidin) was allowed to bind to the immobilized receptor. The bound conjugate was detected with an alkaline phosphatase-labeled, affinity-purified rabbit antibody to fluorescein (Biodesign, Inc., Kennebunkport, Me.). The bound antibody was detected with a standard colorimetric assay for alkaline phosphatase in a microplate reader as described above. Binding of the fluorescein conjugates to the receptor approaches saturation and was substantially (in the case of fl-fucoidin) or completed inhibited (in the case of fl-PPME) by calcium chelation or by MEL-14.

The fluorescein conjugates were prepared by the procedure of Glabe et al., *Anal. Biochem.*, 130:287–294 (1983), which is incorporated herein by reference. Briefly, the polysaccharides were activated by cyanogen bromide treatment and the reacted with fluoresceinamine. Conjugates are then separated from free fluoresceinamine by gel filtration according to standard procedures.

EXAMPLE 3

ELISA Assay with Sulfatide

In this example, the glycolipid sulfatide, was coated onto the wells of a polystyrene microtiter plate by standard absorption procedures. A recombinant LHR conjugate, LHR-IgG (a soluble molecule engineered with a human immunoglobulin Fc region), was allowed to bind to the immobilized sulfatide. The LHR-IgG based upon the LHR for lymph nodes was prepared as described in Watson et al. *J. Cell Biol.* 110:2221–2229 (1990), which is incorporated herein by reference.

The bound recombinant receptor was detected by sequential application of a biotinylated protein A (which reacts with the Fc region) and the alkaline phosphatase-ABC system. The reaction product was measured, as described above, with the microplate ELISA reader. A major component of the signal was inhibited by EGTA (a calcium chelator) or by the MEL-14 antibody.

EXAMPLE 4

Flow Cytometry Assay with fl-PPME or fl-fucoidin

The fluorescein conjugates of PPME and fucoidin (i.e., fl-PPME and fl-fucoidin), described in example 2 above, were used to detect LHR on the surface of viable lymphocytes by flow cytometry. Lymphocytes were exposed to the conjugates, washed, and the amount of conjugate bound to the cell surface was directly determined with a FACSCAN flow cytometer. The majority of lymphocytes reacted with each of the conjugates. The signals were substantially inhibited by EGTA (a calcium chelator) or by the MEL-14 antibody.

EXAMPLE 5

Identification of Surface Glycoproteins on Endothelial Cells Recognized by LHR

This example shows that recombinant LHR selectively binds $^{35}SO_4^-$ labeled macromolecules from lymph nodes. In particular, two sulfated, fucosylated and sialylated glycoproteins have been identified.

A. Metabolic Labeling of Organs with $^{35}$S-sulfate

Mesenteric or peripheral (cervical, brachial, axillary) lymph nodes were collected from 8–16 week old female ICR mice. The lymph nodes were cut into 1 mm thick slices with a razor blade and the slices (typically, 0.2 g of wet weight) were suspended in 1 ml of RPMI-1640 containing 25 mM HEPES, 100 U/ml Penicillin G, 100 μg/ml streptomycin, and 200 μCi carrier-free [$^{35}$S] sodium sulfate (ICN Biochemicals Inc., Costa Mesa, Calif.) according to the procedure of Ager, *J. Cell Sci.*, 87:133–144 (1987) which is incorporated herein by reference. After incubation at 37° C. for 4 hr, the slices were washed extensively in Dulbecco's phosphate-buffered saline (PBS), and then homogenized in 1 ml of lysis buffer (2% Triton X-100 in PBS containing 1 mM PMSF, 1% (v/v) aprotinin, 10 μg/ml pepstatin, 0.02% NaN$_3$) with a Potter-Elvehjem homogenizer on ice.

Lysis was continued for 1 hr on a rocker at 4° C. The lysate was centrifuged at 10,000×g for 1 hr at 4° C. EDTA was added to the supernatant at a final concentration of 2 mm and the supernatant was precleared by rocking with Affi-Gel Protein A (250 μl of packed beads, BioRad Laboratories, Richmond, Calif.) overnight at 4° C.

B. Identification of the Components Adsorbed to LHR-IgG Beads

Affi-Gel Protein A (10 μl packed beads) was incubated with 30 μg of either LHR-IgG (prepared as described above), CD4-IgG (prepaid according to Capon et al., Nature 337:525–531 (1989), which is incorporated herein by reference) or human IgG$_1$ (Calbiochem, La Jolla, Calif.) in 1 ml of PBS rocking overnight at 4° C. The beads (referred to as LHR-IgG beads, CD4-IgG beads and huIgG-beads) were washed 3X in PBS and once with lysis buffer. The CD4-IgG and huIgG beads were used as controls.

The precleared lysate described in Section A, above, was centrifuged at 10,000×g for 10 sec, CaCl$_2$ was added to the supernatant at a final concentration of 5 mM, and the supernatant was mixed immediately with either LHR-IgG beads, CD4-IgG beads or huIgG-beads (typically 200 μl of precleared lysate per 10 μl packed beads), and incubated for 4 hr at 4° C. on a rocker. The beads were washed 6X with lysis buffer, transferred to a new tube, and washed once more with lysis buffer.

The materials bound to the LHR-IgG beads were solubilized by boiling in SDS in the presence of 2-mercaptoethanol, electrophoresed on SDS-polyacrylamide gels (9 or 10%) and subjected to fluorography with ENTENSIFY or EN$^3$HANCE (NEN). By fluorography, the 50 kd component tended to be more diffuse with ENTENSIFY than EN$^3$HANCE. In the reprecipitation experiment, the SDS-solubilized sample was electrophoresed on a 7.5% SDS-gel with prestained standards (BioRad, high range) as markers. The region around 50 kd on the gel was excised by utilizing prestained ovalbumin (49.5 kd) as a position marker, and the protein electroeluted (BioRad model 422) into Laemmli running buffer at 60 mA overnight. The eluate was concentrated and the buffer was exchanged into 10 mM CHAPS in PBS on a Centricon 30 unit (Amicon, Danvers, Mass.), followed by incubation with LHR-IgG beads CD4-IgG or huIgG beads as described above. For the analysis of crude lysate, 200 μl of the precleared lysate was precipitated with cold acetone (80% v/v) and then subjected to electrophoresis as above.

LHR-IgG beads precipitated a diffuse 50 kd component (apparent molecular weight range is 50 kd–58 kd) from [$^{35}$S]-sulfate-labeled mesenteric lymph nodes (MLN) or peripheral lymph nodes (PN). A band of ≈90 kd (83 kd–102 kd), relatively minor in terms of sulfate incorporation, was also observed in most analyses. In control precipitations, CD4-IgG and huIgG beads did not recognize the 50 kd major component or the 90 kd component in the lysates. When crude lysates were directly analyzed, the 50 kd component represented the major constituent among several other bands. The tissue distribution of the 50 kd component was further examined by applying the identical protocol for [$^{35}$S] sulfate-labeling and precipitation with LHR IgG to a number of organs. Among lymphoid tissues, only peripheral lymph nodes and mesentric lymph nodes showed the 50 kd and 90 kd bands, while Peyer's patches, spleen, and thymus were negative for both. Non-lymphoid organs such as kidney, liver, cerebrum, and cerebellum were also completely negative.

LHR-IgG beads precipitated the 50 kd component when calcium was present, but not in its absence. The specificity of the interaction was further examined with the use of MEL-14 mAb. Preincubation of LHR-IgG beads with this antibody completely blocked the binding of the 50 kd band to the beads, whereas a class-matched control antibody (anti-CD45) had no effect. Fucoidin completely blocked the precipitation of the 50 kd component by LHR-IgG beads, while control polysaccharides (chondroitin sulfate B, chondroitin sulfate A, keratan sulfate) were completely inactive. Further, the presence of PPME significantly reduced the intensity of the 50 kd band, although a relatively high concentration was required. A control yeast mannan (mnn 2) had no effect at the same concentration. The precipitation of the minor 90 kd band by LHR-IgG beads was also calcium dependent, inhibitable by MEL-14 mAb, and blocked by fucoidin and PPME.

Finally, sialidase treatment of the glycoproteins was found to inhibit binding by LHR-IgG. Thus, sialic acid on the glycoproteins is apparently essential for binding. This result is in agreement with previous characterizations of interactions between selectins and their ligands.

The examples above demonstrate the ability of the assays of the present invention to identify effective competitive inhibitors of selectin-mediated intercellular adhesion. For the purposes of clarity and understanding, the invention has been described in these examples and the above disclosure in some detail. It will be apparent, however, that certain changes and modifications may be practiced within the scope of the appended claims.

What is claimed is:

1. A method of assaying a test compound for the ability to inhibit intercellular adhesion mediated by a lymphocyte homing receptor, the method comprising the steps of:
    contacting the test compound with an isolated receptor-binding agent and a chimeric molecule comprising a lymphocyte homing receptor component and an immunoglobulin component, the agent being selected from the group consisting of a phosphorylated polysaccharide, a sulfated polysaccharide, a sulfated glycolipid, and a compound comprising the extracellular region of an endothelial cell surface glycoprotein; and
    detecting the ability of the test compound to inhibit binding between the receptor and the agent.

2. A method of claim 1 wherein the receptor is immobilized on a solid surface.

3. A method of claim 1 wherein the step of detecting the binding of the receptor-binding agent to the receptor is carried out using flow cytometry.

4. A method of claim 1 wherein the receptor-binding agent is PPME.

5. A method of claim 1 wherein the receptor-binding agent is fucoidin or dextran sulfate.

6. A method of claim 1 wherein the receptor binding agent is sulfatide.

7. A method of claim 1 wherein the glycoprotein is sgp$^{50}$ or Sgp$^{90}$.

8. A method of claim 1 wherein the receptor-binding agent is labeled.

9. A method of claim 8 wherein the receptor-binding agent is labeled with fluorescein.

10. A method of assaying a carbohydrate test compound for the ability to inhibit intercellular adhesion mediated by a lymphocyte homing receptor, the method comprising the steps of:
- contacting the test compound with a fluoresceinated receptor-binding agent and a lymphocyte; and
- detecting the ability of the test compound to inhibit binding of the receptor-binding agent to the cell using a fluorescence activated flow cytometer.

11. A method of claim 10 wherein the fluoresceinated receptor-binding agent is selected from the group consisting of a sulfated polysaccharide, a sulfated glycolipid, and a compound comprising the extracellular region of an endothelial cell surface glycoprotein.

12. A method of claim 10 wherein the fluoresceinated receptor-binding agent is fucoidin.

13. A method of assaying a test compound for the ability to inhibit intercellular adhesion mediated by a chimeric molecule comprising a lymphocyte homing receptor and an immunoglobulin component, the method comprising the steps of:
- contacting the test compound with a chimeric molecule comprising a lymphocyte homing receptor component and an immunoglobulin component and an isolated receptor-binding agent comprising the extracellular region of an endothelial cell surface glycoprotein selected from the group consisting of $Sgp^{50}$ or $Sgp^{90}$; and
- detecting the ability of the test compound to inhibit binding between the receptor and the agent.

14. A method of claim 13 wherein the receptor is immobilized on a solid surface.

15. A method of claim 13 wherein the receptor-binding agent is labeled.

16. A method of assaying a test compound for the ability to inhibit intercellular adhesion mediated by a lymphocyte homing receptor, the method comprising the steps of:
- immobilizing the test compound on a solid surface;
- contacting the test compound with a chimeric molecule comprising a lymphocyte homing receptor component and an immunoglobulin component; and
- detecting the ability of the lymphocyte homing receptor component of the chimeric molecule to bind to the test compound.

* * * * *